(12) United States Patent
Uchida et al.

(10) Patent No.: US 9,386,968 B2
(45) Date of Patent: Jul. 12, 2016

(54) APPARATUS AND METHODS FOR SEALING A VASCULAR PUNCTURE

(75) Inventors: Andy H. Uchida, Los Altos, CA (US); Kevin To, San Jose, CA (US); Brandon Fell, Menlo Park, CA (US); Peter A. Swenson, San Jose, CA (US)

(73) Assignee: Access Closure, Inc., Santa Clara, CA (US)

( * ) Notice: Subject to any disclaimer, the term of this patent is extended or adjusted under 35 U.S.C. 154(b) by 483 days.

(21) Appl. No.: 13/105,822

(22) Filed: May 11, 2011

(65) Prior Publication Data

US 2012/0290001 A1  Nov. 15, 2012

(51) Int. Cl.
*A61B 17/00* (2006.01)

(52) U.S. Cl.
CPC ..... *A61B 17/0057* (2013.01); *A61B 2017/0065* (2013.01); *A61B 2017/00654* (2013.01); *A61B 2017/00898* (2013.01)

(58) Field of Classification Search
CPC .......... A61B 17/0057; A61B 2017/0575; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/00654; A61B 2017/0065; A61B 2017/00659; A61B 2017/00672; A61B 2017/00898
USPC ................................................ 606/213, 214
See application file for complete search history.

(56) References Cited

U.S. PATENT DOCUMENTS

| | | | |
|---|---|---|---|
| 2,115,492 A | 4/1938 | Kober | |
| 2,365,039 A | 12/1944 | Andresen | |
| 3,765,419 A | 10/1973 | Usher | |
| 4,002,173 A | 1/1977 | Manning | |
| 4,260,077 A | 4/1981 | Schroeder | |
| 4,327,709 A | 5/1982 | Hanson et al. | |
| 4,362,150 A | 12/1982 | Lombardi, Jr. et al. | |
| 4,472,542 A | 9/1984 | Nambu | |
| 4,540,404 A | 9/1985 | Wolvek | |
| 4,654,137 A * | 3/1987 | Vaughan | 204/630 |
| 4,655,211 A | 4/1987 | Sakamoto et al. | |
| 4,664,857 A | 5/1987 | Nambu | |
| 4,734,097 A | 3/1988 | Tanabe | |
| 4,738,658 A | 4/1988 | Magro et al. | |

(Continued)

FOREIGN PATENT DOCUMENTS

| | | |
|---|---|---|
| EP | 0476178 A1 | 3/1992 |
| EP | 0482350 B1 | 4/1992 |

(Continued)

*Primary Examiner* — Dianne Dornbusch
(74) *Attorney, Agent, or Firm* — Nada J. Ardeleanu

(57) ABSTRACT

An apparatus for sealing a puncture through tissue having an introducer sheath therein includes an elongate positioning member including a housing on a proximal end and an expandable member on a distal end, and a cartridge advanceable along the positioning member from a proximal position to a distal position. The cartridge includes a tubular member including a sealant and an advancer member disposed within lumen of the tubular member. A sleeve is slidably disposed over the tubular member distal end such that, when the tubular member is advanced over the positioning member, the tubular member distal end enters the introducer sheath while the sleeve is stopped and slides over the tubular member to expose the tubular member distal end within the introducer sheath. The introducer sheath and cartridge are then withdrawn, exposing the sealant within the puncture.

26 Claims, 9 Drawing Sheets

(56) References Cited

U.S. PATENT DOCUMENTS

| | | |
|---|---|---|
| 4,801,434 A | 1/1989 | Kido et al. |
| 4,838,280 A | 6/1989 | Haaga |
| 4,838,864 A | 6/1989 | Peterson |
| 4,852,568 A | 8/1989 | Kensey |
| 4,890,612 A | 1/1990 | Kensey |
| 5,061,274 A | 10/1991 | Kensey |
| 5,087,246 A | 2/1992 | Smith |
| 5,104,375 A | 4/1992 | Wolf et al. |
| 5,104,389 A | 4/1992 | Deem et al. |
| 5,108,421 A | 4/1992 | Fowler |
| 5,192,300 A | 3/1993 | Fowler |
| 5,192,302 A | 3/1993 | Kensey et al. |
| 5,221,259 A | 6/1993 | Weldon et al. |
| 5,222,974 A | 6/1993 | Kensey et al. |
| 5,258,042 A | 11/1993 | Mehta |
| 5,259,835 A | 11/1993 | Clark et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,324,306 A | 6/1994 | Makower et al. |
| 5,334,216 A | 8/1994 | Vidal |
| 5,370,660 A | 12/1994 | Weinstein |
| 5,383,896 A | 1/1995 | Gershony |
| RE34,866 E | 2/1995 | Kensey et al. |
| 5,391,183 A | 2/1995 | Janzen et al. |
| 5,409,703 A | 4/1995 | McAnalley |
| 5,413,571 A | 5/1995 | Katsaros et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,464,396 A | 11/1995 | Barta et al. |
| 5,486,195 A | 1/1996 | Myers et al. |
| 5,489,278 A | 2/1996 | Abrahamson |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,584,815 A | 12/1996 | Pawelka et al. |
| 5,591,204 A | 1/1997 | Janzen et al. |
| 5,591,205 A | 1/1997 | Fowler |
| 5,601,602 A | 2/1997 | Fowler |
| 5,626,601 A | 5/1997 | Gershony et al. |
| 5,637,086 A | 6/1997 | Ferguson |
| 5,643,464 A | 7/1997 | Rhee |
| 5,660,849 A | 8/1997 | Polson et al. |
| 5,700,477 A | 12/1997 | Rosenthal |
| 5,716,375 A | 2/1998 | Fowler |
| 5,718,916 A | 2/1998 | Scherr |
| 5,725,498 A | 3/1998 | Janzen |
| 5,725,551 A | 3/1998 | Myers et al. |
| 5,728,122 A | 3/1998 | Leschinsky et al. |
| 5,728,132 A | 3/1998 | Van Tassel et al. |
| 5,731,368 A | 3/1998 | Stanley et al. |
| 5,741,223 A | 4/1998 | Janzen et al. |
| 5,744,153 A | 4/1998 | Yewey et al. |
| 5,752,974 A | 5/1998 | Rhee et al. |
| 5,780,044 A | 7/1998 | Yewey et al. |
| 5,782,860 A | 7/1998 | Epstein et al. |
| 5,785,679 A | 7/1998 | Abolfathi et al. |
| 5,795,331 A | 8/1998 | Cragg et al. |
| 5,814,016 A | 9/1998 | Valley |
| 5,830,130 A | 11/1998 | Janzen et al. |
| 5,836,970 A | 11/1998 | Pandit |
| 5,843,124 A | 12/1998 | Hammerslag |
| 5,868,778 A | 2/1999 | Gershony |
| 5,916,236 A | 6/1999 | Muijs Van de Moer et al. |
| 5,922,009 A | 7/1999 | Epstein et al. |
| 5,928,266 A | 7/1999 | Kontos |
| 5,941,847 A | 8/1999 | Huber et al. |
| 5,948,429 A | 9/1999 | Bell |
| 5,948,829 A | 9/1999 | Wallajapet |
| 5,951,583 A | 9/1999 | Jensen et al. |
| 5,951,589 A | 9/1999 | Epstein et al. |
| 5,957,952 A | 9/1999 | Gershony |
| 5,972,375 A | 10/1999 | Truter |
| 5,973,014 A | 10/1999 | Funk |
| 6,017,359 A | 1/2000 | Gershony |
| 6,022,361 A | 2/2000 | Epstein et al. |
| 6,027,471 A | 2/2000 | Fallon et al. |
| 6,045,570 A | 4/2000 | Epstein et al. |
| 6,048,358 A | 4/2000 | Barak |
| 6,051,248 A | 4/2000 | Sawhney |
| 6,056,768 A | 5/2000 | Cates |
| 6,056,769 A | 5/2000 | Epstein et al. |
| 6,063,061 A | 5/2000 | Wallace |
| 6,083,522 A | 7/2000 | Chu |
| 6,090,130 A | 7/2000 | Nash et al. |
| 6,117,145 A | 9/2000 | Wood |
| 6,152,943 A | 11/2000 | Sawhney |
| 6,162,240 B1 | 12/2000 | Cates et al. |
| 6,162,241 B1 | 12/2000 | Coury et al. |
| 6,165,201 A | 12/2000 | Sawhney |
| 6,179,862 B1 | 1/2001 | Sawhney |
| 6,223,936 B1 | 5/2001 | Jeanbourquin |
| 6,238,412 B1 | 5/2001 | Dubrul et al. |
| 6,270,484 B1 * | 8/2001 | Yoon ............................ 604/264 |
| 6,271,278 B1 | 8/2001 | Park |
| 6,287,323 B1 | 9/2001 | Hammerslag |
| 6,296,658 B1 | 10/2001 | Gershony |
| 6,299,597 B1 | 10/2001 | Buscemi et al. |
| 6,302,898 B1 | 10/2001 | Edwards et al. |
| 6,325,789 B1 | 12/2001 | Janzen |
| 6,350,274 B1 | 2/2002 | Li |
| 6,368,300 B1 | 4/2002 | Fallon et al. |
| 6,371,975 B2 | 4/2002 | Cruise et al. |
| 6,379,373 B1 | 4/2002 | Sawhney |
| 6,458,147 B1 | 10/2002 | Cruise et al. |
| 6,464,712 B1 | 10/2002 | Epstein et al. |
| 6,475,177 B1 | 11/2002 | Suzuki |
| 6,514,534 B1 | 2/2003 | Sawhney |
| 6,527,734 B2 * | 3/2003 | Cragg et al. .................... 604/15 |
| 6,540,735 B1 * | 4/2003 | Ashby et al. .................. 604/523 |
| 6,562,059 B2 | 5/2003 | Edwards et al. |
| 6,566,406 B1 | 5/2003 | Pathak |
| 6,569,185 B2 | 5/2003 | Ungs |
| 6,605,294 B2 | 8/2003 | Sawhney |
| 6,608,117 B1 | 8/2003 | Gvozdic |
| 6,610,026 B2 | 8/2003 | Cragg |
| 6,613,070 B2 | 9/2003 | Redmond et al. |
| 6,626,861 B1 | 9/2003 | Hart |
| 6,626,918 B1 | 9/2003 | Ginn |
| 6,635,068 B1 | 10/2003 | Dubrul et al. |
| 6,689,148 B2 | 2/2004 | Sawhney |
| 6,699,261 B1 | 3/2004 | Cates et al. |
| 6,703,047 B2 | 3/2004 | Sawhney |
| 6,774,151 B2 | 8/2004 | Malmgren |
| 6,818,008 B1 * | 11/2004 | Cates et al. .................... 606/213 |
| 6,818,018 B1 | 11/2004 | Sawhney |
| 6,863,924 B2 | 3/2005 | Ranganathan |
| 6,887,974 B2 | 5/2005 | Pathak |
| 6,890,342 B2 | 5/2005 | Zhu et al. |
| 6,890,343 B2 | 5/2005 | Ginn et al. |
| 6,899,727 B2 * | 5/2005 | Armstrong et al. .......... 623/1.12 |
| 6,960,617 B2 | 11/2005 | Omidian |
| 6,994,686 B2 | 2/2006 | Cruise et al. |
| 7,009,034 B2 | 3/2006 | Pathak |
| 7,331,979 B2 | 2/2008 | Khosravi |
| 7,335,220 B2 | 2/2008 | Khosravi |
| 7,611,479 B2 | 11/2009 | Cragg et al. |
| 7,621,936 B2 | 11/2009 | Cragg et al. |
| 7,790,192 B2 | 9/2010 | Sawhney et al. |
| 7,806,856 B2 | 10/2010 | Bagaoisan |
| 7,806,903 B2 * | 10/2010 | Shibata et al. ................ 606/142 |
| 7,850,710 B2 | 12/2010 | Huss |
| 7,955,353 B1 | 6/2011 | Ashby et al. |
| 7,993,367 B2 * | 8/2011 | Bagaoisan et al. ............ 606/213 |
| 8,029,533 B2 * | 10/2011 | Bagaoisan et al. ............ 606/213 |
| 8,128,654 B2 * | 3/2012 | Khosravi et al. .............. 606/213 |

(56) References Cited

U.S. PATENT DOCUMENTS

| | | |
|---|---|---|
| 8,382,797 B2 * | 2/2013 | Khosravi et al. .............. 606/213 |
| 8,382,798 B2 * | 2/2013 | Khosravi et al. .............. 606/213 |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney et al. |
| 2002/0111392 A1 | 8/2002 | Cruise |
| 2002/0111651 A1 | 8/2002 | Ungs |
| 2002/0188319 A1 | 12/2002 | Morris et al. |
| 2002/0193808 A1 | 12/2002 | Belef |
| 2003/0008831 A1 | 1/2003 | Yang et al. |
| 2003/0012734 A1 | 1/2003 | Pathak |
| 2003/0051735 A1 | 3/2003 | Pavcnik et al. |
| 2003/0088269 A1 | 5/2003 | Ashby |
| 2003/0088271 A1 | 5/2003 | Cragg et al. |
| 2003/0135234 A1 | 7/2003 | Fisher et al. |
| 2003/0135235 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeldt |
| 2004/0122350 A1 | 6/2004 | Zhong et al. |
| 2004/0143290 A1 | 7/2004 | Brightbill |
| 2004/0147016 A1 | 7/2004 | Rowley |
| 2004/0236262 A1 | 11/2004 | McIntosh et al. |
| 2004/0267308 A1 * | 12/2004 | Bagaoisan et al. ............ 606/213 |
| 2005/0085852 A1 * | 4/2005 | Ditter ............................ 606/213 |
| 2006/0015171 A1 * | 1/2006 | Armstrong .................... 623/1.12 |
| 2006/0034930 A1 * | 2/2006 | Khosravi et al. .............. 424/484 |
| 2006/0100664 A1 * | 5/2006 | Pai et al. ....................... 606/214 |
| 2006/0253037 A1 | 11/2006 | Ginn |
| 2006/0253072 A1 | 11/2006 | Pai |
| 2007/0060950 A1 | 3/2007 | Khosravi |
| 2007/0135837 A1 * | 6/2007 | Yassinzadeh ................. 606/214 |
| 2007/0231366 A1 | 10/2007 | Sawhney |
| 2008/0097521 A1 * | 4/2008 | Khosravi et al. .............. 606/213 |
| 2009/0088793 A1 * | 4/2009 | Bagaoisan et al. ............ 606/213 |
| 2009/0254110 A1 * | 10/2009 | Bagaoisan et al. ............ 606/185 |
| 2010/0168767 A1 * | 7/2010 | Yassinzadeh et al. ......... 606/139 |
| 2010/0168789 A1 * | 7/2010 | Bagaoisan et al. ............ 606/213 |
| 2010/0211000 A1 | 8/2010 | Killion et al. |
| 2010/0234726 A1 * | 9/2010 | Sirimanne et al. ............ 600/426 |
| 2012/0089177 A1 * | 4/2012 | Tegels .......................... 606/213 |

FOREIGN PATENT DOCUMENTS

| | | |
|---|---|---|
| EP | 0716833 | 6/1996 |
| WO | 9222252 | 12/1992 |
| WO | 9413210 A1 | 6/1994 |
| WO | 9428798 | 12/1994 |
| WO | 9922646 A1 | 5/1999 |
| WO | 0014155 | 3/2000 |
| WO | 0019912 | 4/2000 |
| WO | 03009764 A1 | 2/2003 |
| WO | 03087254 A2 | 10/2003 |
| WO | 03004749 | 11/2003 |

* cited by examiner

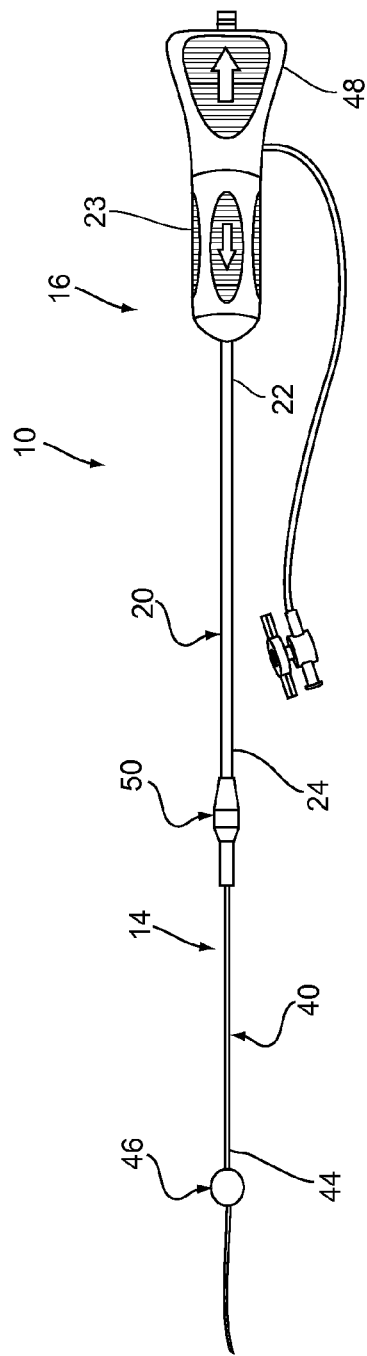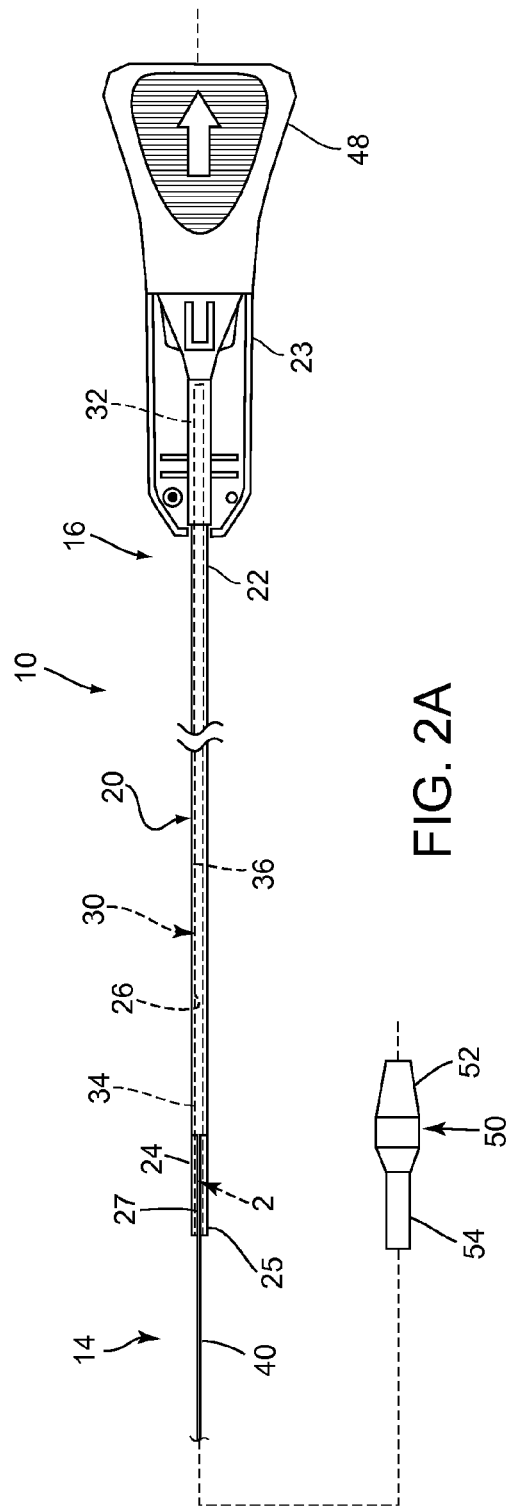

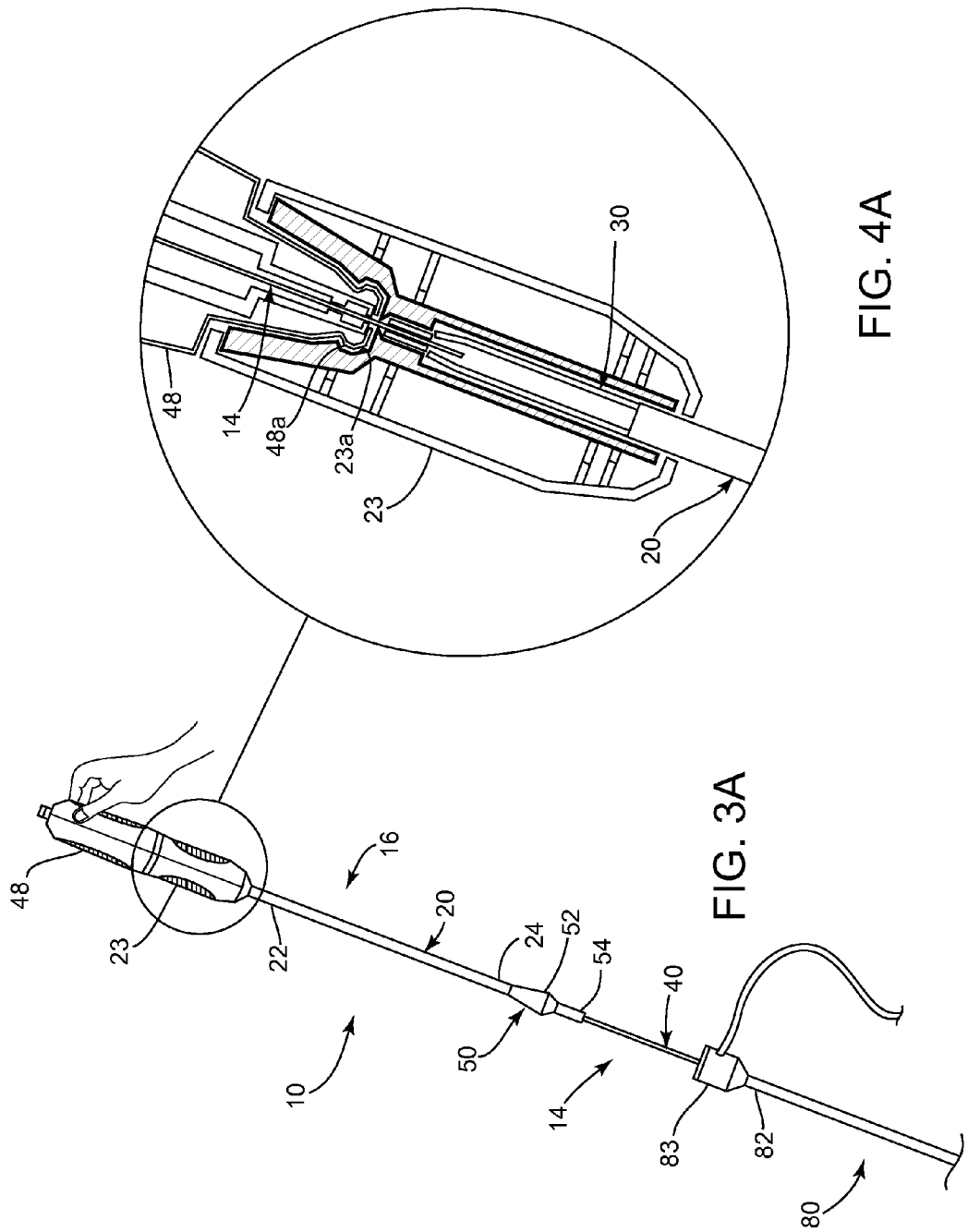

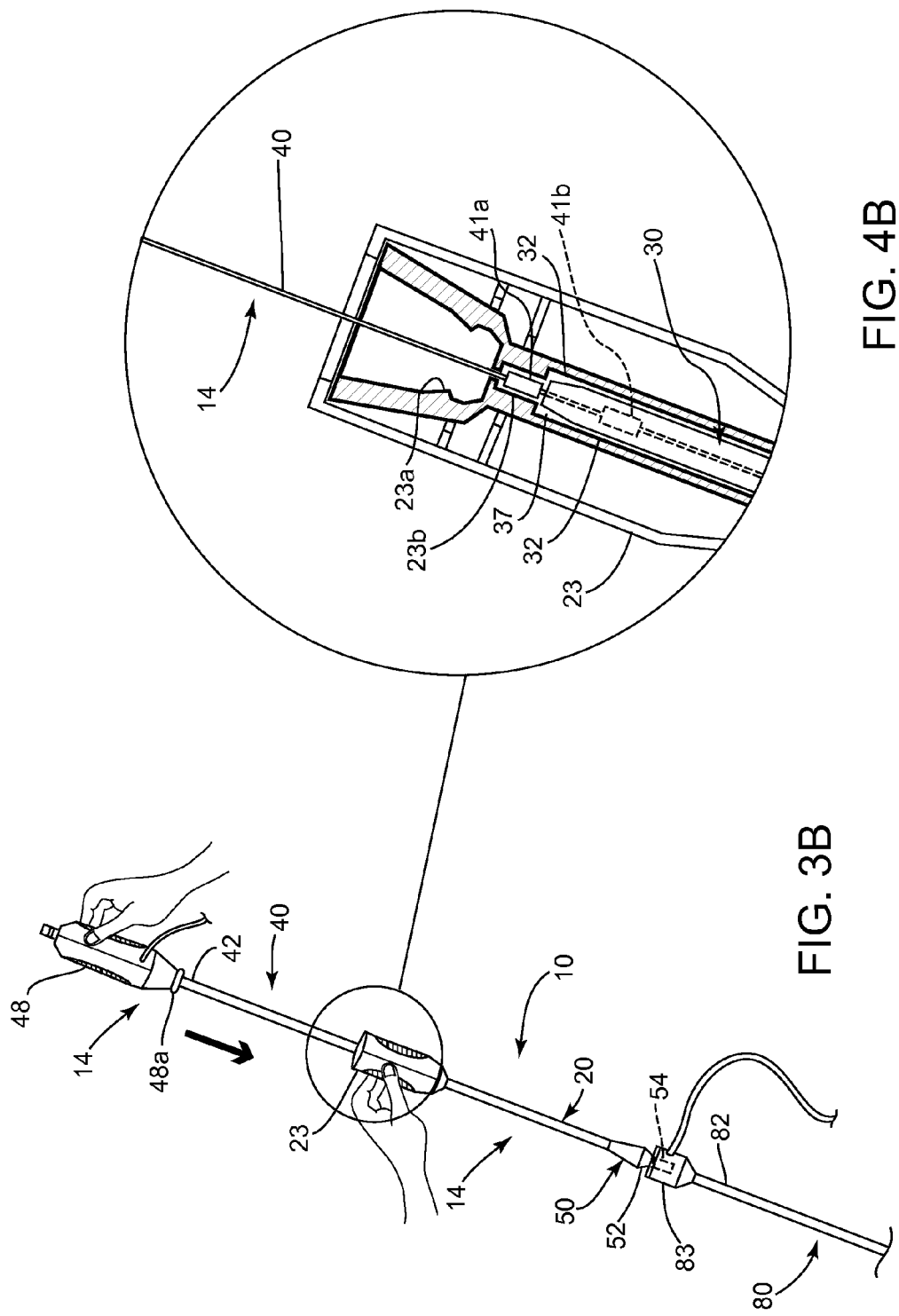

APPARATUS AND METHODS FOR SEALING A VASCULAR PUNCTURE

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug, sealant, and/or other material into a percutaneous puncture extending from a patient's skin to a blood vessel or other body lumen, e.g., to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a plug that may be delivered into a puncture through tissue. U.S. Pat. Nos. 5,192,302 and 5,222,974 issued to Kensey et al. describe a bioabsorbable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

U.S. Pat. No. 6,605,294 describes rods, plugs, and crushed or irregularly shaped pieces of substantially dehydrated hydrogel that may be introduced into a lumen or void in a patient's body, e.g., to seal or plug a biopsy needle track, reinforce weak tissue, or deliver a therapeutic compound. In one embodiment, a plug of dehydrated hydrogel may be deployed into the site of an arteriotomy and allowed to hydrate in the presence of the tissue fluids and blood, to fill the tract of the catheter sheath and prevent further bleeding. By swelling to equilibrium hydration, the plug may lock itself firmly in place and thus reduce the risk of formation of a large hematoma at the site of the puncture.

U.S. Pat. No. 6,703,047 discloses dehydrated hydrogel precursor-based, tissue adherent compositions. The hydrogels may be used, for example, for sealing fluid leaks from tissue, as adherent drug delivery depots, and as means for augmenting and/or supporting tissue. The hydrogels may be administered directly to an open wound site or may be dispensed, e.g., using a non-adhesive backing material, an absorbable backing material, a syringe applicator, a powder atomization or aerosolization system, or a needle-less injector.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealant and/or other material into a percutaneous puncture extending from a patient's skin to a blood vessel or other body lumen.

In accordance with one embodiment, an apparatus is provided for sealing a puncture extending through tissue having an introducer sheath therein that includes a proximal end including a hub, a distal end, and a lumen extending therebetween. The apparatus includes an elongate positioning member including a housing on a proximal end thereof, and an expandable positioning element on a distal end thereof, and a cartridge advanceable along the positioning member from a proximal position adjacent the housing to a distal position. The cartridge may include a tubular member, a sealant disposed within a lumen of the tubular member, e.g., adjacent the tubular member distal end, and an advancer member disposed within the tubular member lumen adjacent the sealant, e.g., for exposing the sealant from the tubular member lumen when the tubular member is retracted proximally relative to the advancer member.

In addition, the cartridge includes a sleeve slidably disposed over the tubular member distal end, e.g., covering a slitted distal tip of the tubular member. Optionally, the sleeve may include an inner surface configured to provide preferential or different frictional interference with an outer surface of the tubular member, e.g., to allow proximal movement and resist distal movement of the sleeve over the tubular member. At least a portion of the sleeve may be sized to abut the introducer sheath hub such that, when the tubular member is advanced from the proximal position to the distal position, the tubular member distal end enters the introducer sheath lumen while the sleeve is stopped by the introducer sheath hub and slides over the tubular member to expose the tubular member distal end within the introducer sheath lumen.

For example, in one embodiment, the sleeve may include a distal portion sized to enter the introducer sheath hub when the cartridge is advanced towards the distal position and a proximal portion that abuts the introducer sheath hub to prevent the entire sleeve from entering the introducer sheath lumen. The introducer sheath hub may include a valve therein, and the sleeve distal portion may at least partially open the valve when the cartridge is advanced towards the distal position, e.g., to facilitate the tubular member distal end entering the introducer sheath lumen.

Optionally, the positioning member and/or cartridge may include one or more features that limit distal movement of the tubular member when the cartridge is advanced from the proximal position to the distal position. For example, features may be provided on the positioning member to prevent further distal movement of the tubular member when the tubular member distal end is spaced a predetermined distance from the positioning element.

In accordance with another embodiment, a system is provided for sealing a puncture through tissue that generally includes an introducer sheath, a positioning member, and a cartridge. The introducer sheath may include a proximal end including a hub, a distal end sized for introduction into a puncture, and a lumen extending therebetween. The positioning member may include an elongate member including a housing on a proximal end thereof and an expandable positioning element on a distal end thereof. The cartridge may be advanceable along the positioning member from a proximal position to a distal position, and may include a tubular member including a sealant and an advancer member disposed within lumen of the tubular member. A sleeve is slidably disposed over the tubular member distal end such that, when the tubular member is advanced over the positioning member after introducing the positioning element through the introducer sheath, the tubular member distal end enters the introducer sheath lumen while the sleeve is stopped by the introducer sheath hub and slides over the tubular member to expose the tubular member distal end within the introducer sheath lumen.

In accordance with still another embodiment, a method is provided for sealing a puncture extending through tissue to a body lumen, the puncture having an introducer sheath therein. An apparatus may be provided including an elongate positioning member including proximal and distal ends, a cartridge slidable on the positioning member and carrying a sealant therein, and a slidable sleeve located over a distal end of the cartridge.

The distal end of the positioning member may be introduced through a lumen of the introducer sheath until a positioning element thereon is disposed within the body lumen. Optionally, the positioning element may be expanded within the body lumen, and the positioning member may be refracted until the expanded positioning element contacts a wall of the body lumen.

The cartridge may be advanced over the positioning member, e.g., until the sleeve on the cartridge contacts a proximal end of the introducer sheath. The cartridge may be advanced further, e.g., as one substantially continuous movement, such that the cartridge distal end enters the introducer sheath lumen while the sleeve is stopped by the introducer sheath. During this further advancement, the sleeve may slide over the cartridge to expose the cartridge distal end within the introducer sheath lumen, e.g., until a distal position is attained.

The introducer sheath and cartridge may then be at least partially retracted from the puncture, thereby exposing the sealant within the puncture distally beyond the introducer sheath. The expanded positioning element may then be collapsed, and the positioning member withdrawn from the puncture, e.g., leaving the sealant within the puncture. In one embodiment, the cartridge may include an advancer member adjacent the sealant that remains within the puncture when the introducer sheath and cartridge are retracted. In this embodiment, the positioning member may be withdrawn through the sealant and advancer member. For example, the advancer member may be held substantially stationary while the positioning member is withdrawn from the puncture to prevent substantial proximal movement of the sealant. In addition or alternatively, the advancer member may be advanced to compress the sealant within the puncture, e.g., before or after withdrawing the positioning member. The advancer member may then be withdrawn, leaving the sealant within the puncture.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 1A and 1B are side and perspective views, respectively, of an exemplary embodiment of an apparatus for delivering a sealant into a puncture through tissue, including a positioning member, and a cartridge movable over the positioning member that includes the sealant and a slidable sleeve.

FIG. 2A is a partial cross-section of the apparatus of FIGS. 1A and 1B before the slidable sleeve is directed over a distal end of the cartridge.

FIGS. 3A and 3B are side views of the apparatus of FIGS. 1A and 1B with the positioning member inserted into an introducer sheath, showing the cartridge in proximal and distal positions, proximally.

FIGS. 4A and 4B are cross-sectional views of a housing on the cartridge of the apparatus of FIGS. 3A and 3B, with the cartridge in proximal and distal positions, respectively.

DETAILED DESCRIPTION OF THE EXEMPLARY EMBODIMENTS

Figure 1B:
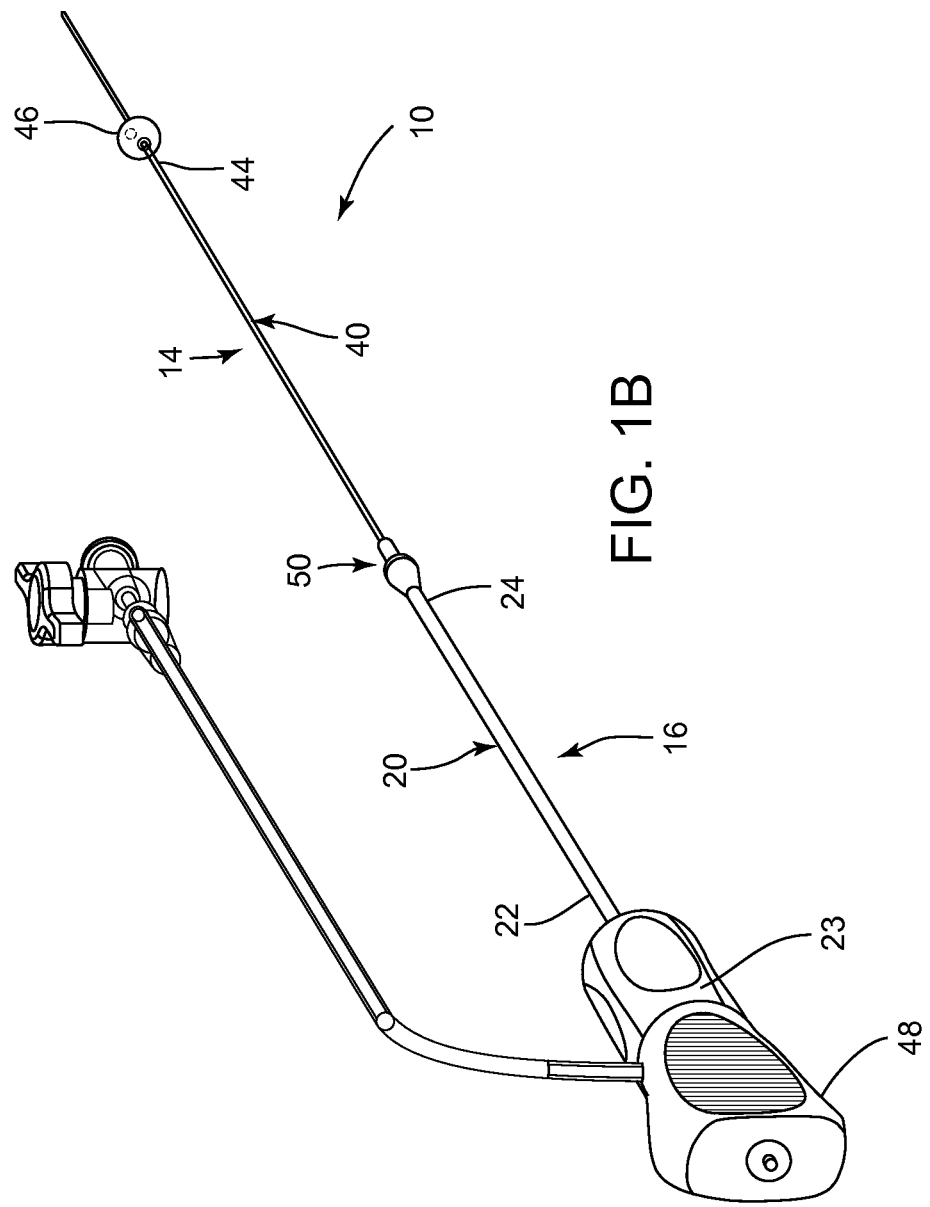

Turning to the drawings, FIGS. 1A and 1B show an exemplary embodiment of an apparatus 10 for sealing a puncture through tissue. Generally, the apparatus 10 includes a positioning member 14 and a cartridge 16 carried on the positioning member 14 for delivering a sealant 2 therein into a puncture (not shown). As shown in FIGS. 3A and 3B, the apparatus 10 may be part of a system, e.g., which may also include a delivery, access, procedure, introducer, or other sheath 80. Optionally, the apparatus 10 and/or system may include one or more other components, e.g., a needle, guidewire, and/or other instrument for creating a puncture (not shown), and/or a source of additional sealing compound (also not shown).

As best seen in FIG. 2A, the cartridge 16 includes an elongate tubular member 20 carrying the sealant 2 therein, an advancer member 30 adjacent the sealant 2, and a slidable sleeve or cover 50, as described further below. Generally, the tubular member 20 includes a proximal end 22, a distal end 24 sized for introduction into an introducer sheath and/or puncture (not shown), and a lumen 26 extending between the proximal and distal ends 22, 24. The tubular member 20 may be substantially rigid, semi-rigid, or flexible, e.g., such that the tubular member 20 may be advanced through an introducer sheath or otherwise into a puncture through tissue. A handle or hub 23 may be provided on the proximal end 22, e.g., for releasably coupling the cartridge 16 to the positioning member 14, as best seen in FIGS. 4A and 4B and described further below.

As shown in FIG. 2A, a distal tip 25 of the tubular member 20 may be split, e.g., including one or more slits or other features 27, e.g., to facilitate exposing the sealant 2 from the cartridge 16. For example, a split distal tip 25 may facilitate retraction of the tubular member 20 relative to the sealant 2, e.g., by providing extra flexibility at the distal end 24 and/or allowing the distal end 24 to expand or otherwise open slightly. This may allow the distal end 24 to separate more easily from the sealant 2, e.g., as the sealant begins to expand upon being exposed to an aqueous environment, which may reduce the risk of the sealant 2 binding up within or otherwise resisting exposure from the lumen 26 of the tubular member 20.

In addition, the slits 27 may accommodate slight expansion of the sealant 2 before being exposed from the tubular member 20. For example, a distal surface of the sealant 2 may be exposed to bodily fluids when the cartridge 16 is advanced into a puncture, which may hydrate and cause the distal end of the sealant 2 to expand slightly. Optionally, the distal end 24 of the tubular member 20 may be exposed to water or other fluid before use of the apparatus 10, e.g., to partially hydrate the distal end of the sealant 2 and cause the distal end to expand slightly. The slits 27 may allow the distal end 24 of the tubular member 20 to open to accommodate such expansion. Otherwise, if the sealant 2 hydrates and/or otherwise expands within the tubular member 20, the sealant 2 may impose radially outward forces, which may hinder retracting the tubular member 20 to expose the sealant 2.

In the exemplary embodiment shown, a single longitudinal slit 27 is cut or otherwise formed on one side of the distal tip 25 that extends proximally from the distal tip 25, e.g., about ten to twenty millimeters (10-20 mm). Alternatively, a pair of slits may be provided, e.g., on opposite sides of the distal tip 25 or more than two slits may be provided, if desired (not shown). The length of the slit(s) may be less than, substantially equal to, or longer than the length of the sealant 2, e.g., to reduce the risk of jamming if the sealant 2 begins to expand within the distal tip 25, as described elsewhere herein.

A slit that is longer than the sealant 2 may provide hydraulic benefits, e.g., when the cartridge 16 is advanced to introduce the sealant 2 into a puncture. For example, during use, as the cartridge 16 is advanced into an introducer sheath (not shown), as described further below, fluid inside the introducer sheath may be displaced distally by the cartridge 16, which may increase pressure at the distal end 24 of the tubular member 20 and/or introducer sheath. This increased hydraulic pressure at the distal end 24 of the tubular member 20 may also transmit along the sides of the cartridge 16, e.g., if there is a gap between the inner diameter of the introducer sheath and the outer diameter of the tubular member 20. A longer slit 27 may allow some relief of this pressure, e.g., by blood or other fluid within the introducer sheath flowing in directly behind the sealant 2 within the lumen 26 of the tubular member 20 and/or otherwise within the cartridge 16. Such infusion behind the sealant 2 may also have the benefit of pre-hydrating the sealant 2, which may enhance the ability of the sealant 2 to expand quickly when deployed within a puncture or otherwise within the patient's body.

With further reference to FIG. 2A, the advancer member 30 may be an elongate tubular body, e.g., a plunger or catheter, including a proximal end 32, a distal end 34 sized for introduction into the lumen 26 of the tubular member 20, and a lumen 36 extending between the proximal and distal ends 32, 34. The advancer member 30 may be sized for being slidably received within the lumen 26 of the tubular member 20, although the advancer member 30 may abut or otherwise interact with the hub 23 of the cartridge 16, e.g., such that the advancer member 30 is advanced distally when the cartridge 16 is advanced. The distal end 34 of the advancer member 30 may terminate in a substantially blunt distal tip, e.g., to facilitate contacting, pushing, and/or maintaining the sealant 2 within a puncture, as described further below.

The advancer member 30 may be substantially rigid, semi-rigid, and/or substantially flexible, having sufficient column strength to allow proximal movement of the tubular member 20 relative to the sealant 2 without buckling the advancer member 30 and/or to allow the distal end 34 of the advancer member 30 to be advanced to compress the sealant 2 within a puncture, e.g., by pushing from the proximal end 32, as described further below. The advancer member 30 may also include a lumen 36 extending between the proximal and distal ends 32, 34, e.g., to accommodate the positioning member 14, a guidewire, a flowable sealing compound, and/or fluid (not shown).

Optionally, the advancer member 30 may include one or more elements (not shown) on the proximal end 32, e.g., for interacting with one or more cooperating elements (also not shown) on the positioning member 14, e.g., to limit movement of the advancer member 30 relative to the positioning member 14. For example, the element(s) may simply be a relatively narrow region (not shown) on the proximal end 32. Alternatively, the element(s) may be a separate collar or sleeve, one or more inwardly oriented detents, and the like (also not shown) attached to or otherwise formed on the proximal end 32 of the advancer member 30.

The sealant 2 may be disposed within the lumen 26 of the tubular member 20 proximate to the distal end 24, e.g., immediately adjacent the distal tip 25, as shown in FIG. 2A. The lumen 26 may be sized such that the tubular member 20 and sealant 2 are slidable relative to one another, e.g., to allow the tubular member 20 to be retracted proximally relative to the sealant 2 and/or advancer member 30, as described further below.

The sealant 2 may include a biocompatible, bioabsorbable, and/or expandable material, such as a freeze-dried hydrogel. The sealant 2 may have a solid or hollow cylindrical shape, a rolled sheet shape, a disk shape, or other shapes or cross-sections, such as elliptical, triangular, square, conical, disk, polygonic shapes. For example, the sealant 2 may be formed from a solid material including a lumen (not shown) extending between proximal and distal ends thereof. The lumen may be created by rolling a sheet of material around a mandrel, by molding, by boring into or otherwise removing material from an already formed solid material, and the like. The lumen may be dimensioned such that the positioning member 14, a guidewire or other instrument (not shown) may slide or otherwise pass through the sealant 2, as described elsewhere herein.

In one embodiment, the sealant 2 may be formed from a biocompatible and/or bioabsorbable hydrogel, e.g., polyethylene glycol ("PEG"), or other synthetic material. For example, the hydrogel may include a lyophilized (i.e., freeze-dried) PEG polymer that includes hydrolytically degradable chemical groups, e.g., including a macroporous polymer network, which may uptake fluid and expand when exposed to an aqueous environment. The magnitude of expansion or swelling (pre to post hydration) may be significant, e.g., between about two and ten times (2×-10×) its lyophilized size based on volume.

In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like.

Optionally, the sealant 2 may include one or more therapeutic and/or pharmaceutical agents, e.g., to promote healing, prevent infection and/or other adverse medical events, and the like. Such agents may be embedded in the sealant material and/or applied as one or more coatings or layers. In addition or alternatively, the sealant 2 may be substantially homogeneous, or may include one or more different materials at one or more locations. For example, in one embodiment, the sealant 2 may include a carrier or core having first and second hydrogel precursors disposed thereon in an unreactive state, which may provide an adherent coating when the sealant 2 is exposed to an aqueous environment.

Exemplary materials and methods for making and using them are disclosed in U.S. Pat. Nos. 6,152,943, 6,165,201, 6,179,862, 6,514,534, 6,379,373, 6,703,047, 7,790,192, and in co-pending application Ser. Nos. 10/010,715 filed Nov. 9, 2001, 10/068,807 filed Feb. 5, 2002, 10/454,362, filed Jun. 4, 2003, published as US 2004/0249342, 10/982,384, filed Nov. 5, 2004, published as US 2006/0099238, and 11/465,791, filed Aug. 18, 2006. The disclosures of these references are expressly incorporated by reference herein.

Additionally, as shown in FIGS. 1A and 1B, the cartridge 16 includes a sleeve or cover 50 slidably disposed over the tubular member 20, e.g., for covering the distal end 24 before use and/or advancement of the cartridge 16. For example, the sleeve 50 may support the distal end 24, e.g., by covering the distal tip 25 and preventing premature expansion or separation of the slits 27, e.g., before the distal end 24 is exposed from the sleeve 50, as described further below.

Figure 2B:
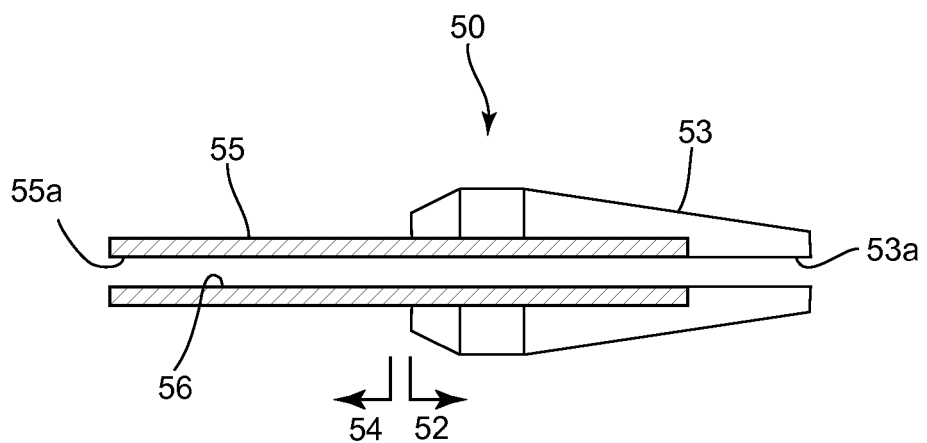
FIG. 2B is a cross-sectional detail of the sleeve of FIG. 2A.

As best seen in FIGS. 2A and 2B, the sleeve 50 may include a relatively large diameter proximal portion 52, e.g., sized to abut or otherwise contact a hub or proximal end of an introducer sheath (not shown), and a relatively small diameter distal portion 54, e.g., sized to enter the hub and/or lumen of the introducer sheath (not shown). For example, the introducer sheath hub may include one or more valves, e.g., a hemostatic valve therein, and the sleeve distal portion 54 may be sized to enter the hub and at least partially open the valve when the cartridge 16 is advanced, e.g., to facilitate the distal end 24 of the tubular member 20 entering the introducer sheath lumen, as described further below.

The sleeve 50 may have a relatively short length compared to the tubular member 20, e.g., such that the sleeve 50 may slide proximally over the tubular member 20 a desired distance. For example, the sleeve 50 may have an overall length between about twelve and twenty four millimeters (12-24 mm), and the distal portion 54 may have a length, e.g., between about three and twenty millimeters (3-20 mm).

Optionally, the sleeve 50 may include an inner lumen 56 configured to provide preferential and/or different frictional interference with an outer surface of the tubular member 20. For example, the inner lumen 56 may allow the sleeve 50 to slide freely proximally relative to the tubular member 20, while providing enhanced friction that resists distal movement of the sleeve 50 over the tubular member 20. In addition or alternatively, the sleeve 50 may be releasably attached to the cartridge 16, e.g., using a low bond adhesive, and the like, which may be released or otherwise overcome when the cartridge 16 is advanced into an introducer sheath, as described further below.

In an exemplary embodiment, shown in FIG. 2B, the sleeve 50 may be formed from an outer annular body 53 defining the proximal portion 52, and a section of tubing 55 at least partially received within the annular portion 53, e.g., defining the distal portion 54. The components of the sleeve 50 may be made from the same or different materials, e.g., plastic, metal, or composite materials. For example, the tubing 55 may be formed from substantially rigid plastic, such as polyimide, and the annular body 53 may be formed from polyether block amide (PEBAX), polyurethane, silicone, or other relatively soft durometer materials. The components may be attached to one another, e.g., by bonding with adhesive, ultrasonic welding, fusing, melting, and the like.

As best seen in FIG. 2B, an annular portion 53a of the annular body 53 and the tubing 55 together define the lumen 56 that extends through the sleeve 50. The lumen 56 may be sized to allow the sleeve 50 to slide over the tubular member 20 (not shown, see, e.g., FIGS. 1A-2A), e.g., while providing a slight interference. For example, the annular portion 53a adjacent the tubing 55 may have an inner diameter slightly smaller than the inner diameter 55a of the tubing 55, such that, when the sleeve 50 is directed proximally over the tubular member 20 (e.g., when the tubular member 20 is advanced distally relative to the sleeve 50), the soft durometer material of the annular portion 53a may bunch up slightly, thereby expanding the size of the lumen 56 and reducing frictional interference between the sleeve 50 and the tubular member 20. Conversely, if the sleeve 50 is directed distally over the tubular member 20 (or the tubular member 20 is directed proximally relative to the sleeve 50), the annular portion 53a surrounding the lumen 56 may stretch slightly, thereby reducing the size of the lumen 56 within the annular portion 53a and increasing frictional interference between the annular portion 53a of the sleeve 50 and the tubular member 20. In this manner, the sleeve 50 may slide freely proximally while being substantially prevented from sliding distally over the tubular member 20.

Returning to FIGS. 1A and 1B, the positioning member 14 generally includes an elongate member 40 including a proximal end 42 (not shown, see, e.g., FIG. 3B), a distal end 44, and an occlusion or positioning element 46 on the distal end 44. The positioning element 46 may be an expandable member, such as a balloon, a wire mesh structure, an expandable frame, and the like. The positioning element 46 may be selectively expandable, e.g., using a source of inflation media, a pull wire, and/or other actuator (not shown), operable from the proximal end 42 of the positioning member 14.

For example, as shown, the positioning element may be a balloon 46, and the positioning member 14 may include a tubular body 40 including a lumen (not shown) extending between the proximal and distal ends 42, 44 and communicating with an interior of the balloon 46. In this embodiment, the positioning member 14 may include a source of inflation media, e.g., a syringe (not shown), that may be coupled to a housing 48 on the proximal end 142 of the positioning member 14. Optionally, the positioning member 14 may include an internal pull wire (not shown) that causes the balloon 46 to shorten during expansion and extend during collapse. Exemplary embodiments of positioning members 14 including balloons that may be used are disclosed in co-pending applications Ser. No. 10/454,362, filed Jun. 4, 2003, published as US 2004/0249342, Ser. No. 11/112,877, filed Apr. 22, 2005, published as US 2006/0253072, and Ser. No. 11/112,971, filed Apr. 22, 2005, and published international application WO 2006/115904. The entire disclosures of these references are expressly incorporated by reference herein.

Alternatively, the positioning element may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 14 may be found in U.S. Pat. Nos. 6,238, 412, 6,635,068, and 6,890,343, and in co-pending application Ser. No. 10/975,205, filed Oct. 27, 2004. The entire disclosures of these references are expressly incorporated herein by reference.

Figure 5A:
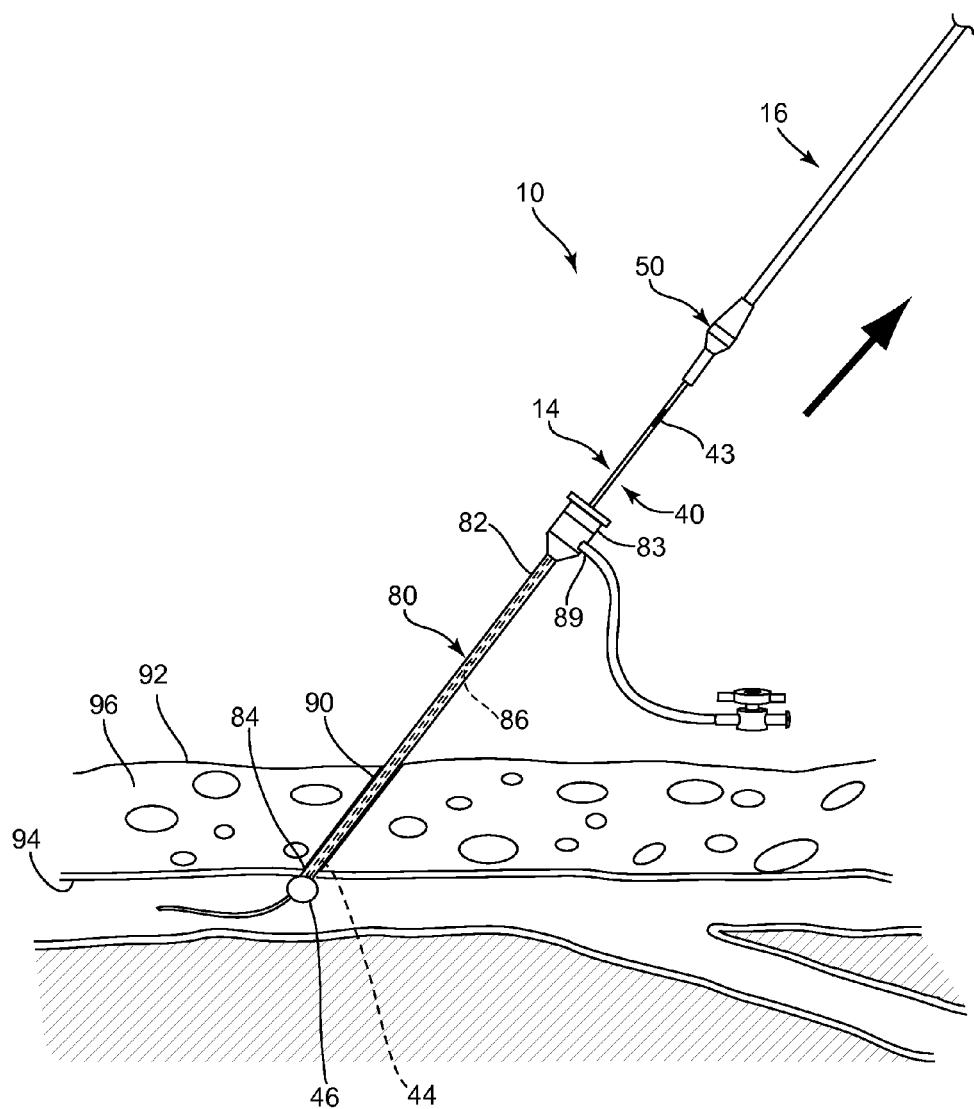
FIGS. 5A-5D are cross-sectional views of a patient's body, showing a method for sealing a puncture extending from a patient's skin to a blood vessel using the apparatus of FIGS. 1A and 1B.
Figure 5B:
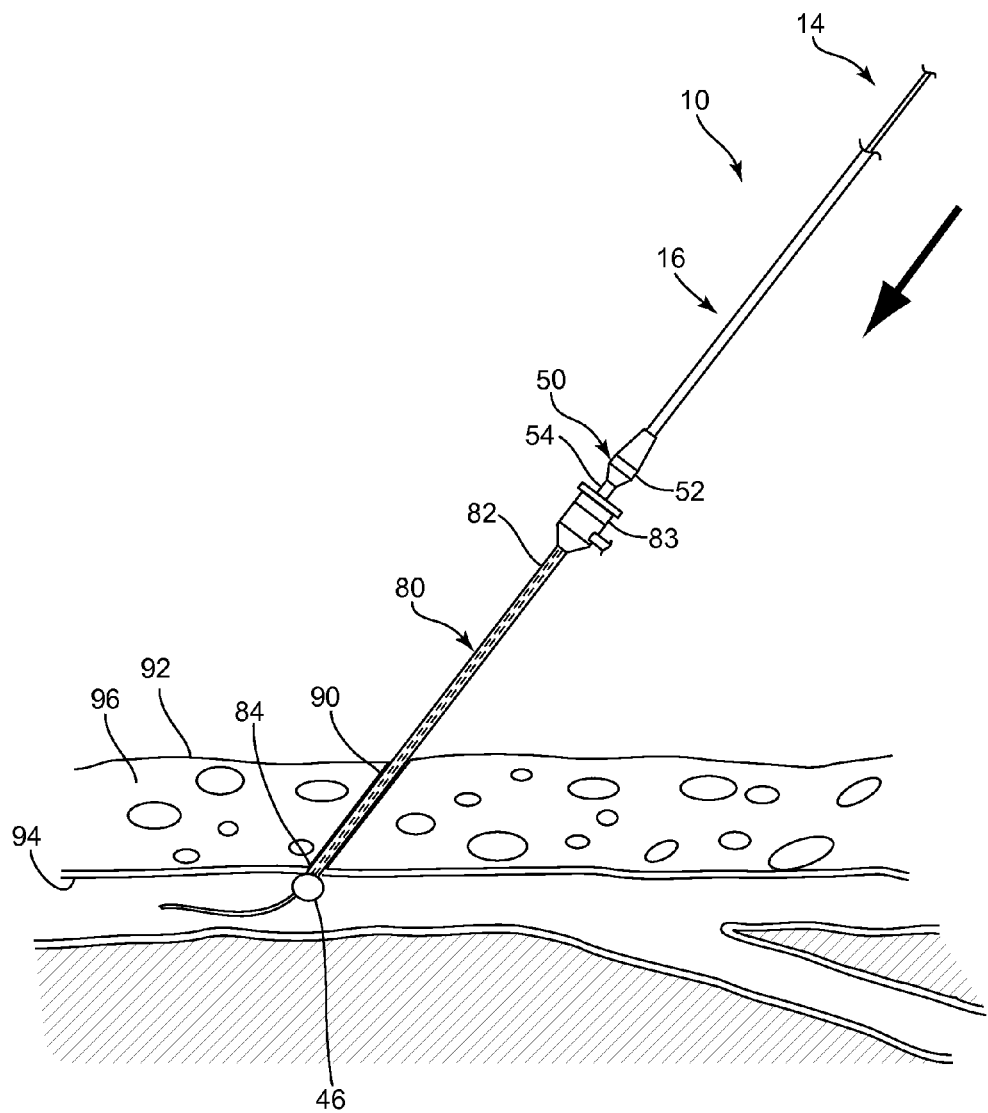

Turning to FIGS. 5A-5B, the apparatus 10 may be used to position and deliver the sealant 2 within a puncture, e.g., extra-vascularly just above or otherwise adjacent to an arteriotomy in a blood vessel or other body lumen communicating with a puncture, as described further elsewhere herein. In one embodiment, as shown in FIG. 3A, the cartridge 16 (along with the advancer member 30 and sealant 2 within the tubular member 20) may be initially provided on the proximal end 42 of the positioning member 14. For example, the housing 48 on the positioning member 14 and the hub 23 on the cartridge 16 may be initially connected to one another, e.g., using one or more releasable detents 23a, 48a, as shown in FIG. 4A.

As shown in FIG. 3B, the cartridge 16 may be slidable distally along the positioning member 14, e.g., by disconnecting the hub 23 from the housing 48, and then advancing the cartridge 16, e.g., until the distal end 24 of the tubular member 20 is disposed adjacent the positioning element 46. For example, the detents 23a, 48a may simply separate from one another when the hub 23 is advanced away from the housing 48 with sufficient force. Alternatively, one of the hub 23 and housing 48 may include an actuator or lock that may be activated (not shown) to separate the detents 23a, 48a and/or otherwise allow the cartridge 16 to be advanced relative to the positioning member 14.

Optionally, the cartridge 16 and/or positioning member 14 may include cooperating features that limit distal movement of the cartridge 16 relative to the positioning member 14. For example, as shown in FIG. 4B, the hub 23 of the cartridge 16 may include a pocket 23b and the positioning member 14 may include a detent or other feature 41a that may be received within the pocket 23b when the cartridge 16 is advanced to a distal position. Optionally, the handle 23 of the cartridge 16 may include a window or other opening (not shown) through which the pocket 23b may be seen, e.g., to allow a user to visually confirm when the detent 41 has been fully received in the pocket 23b.

The detent 41a may be provided on the outer surface of the elongate member 40 at a predetermined location between the proximal and distal ends 42, 44 such that the distal end 24 of the tubular member 20 is spaced apart from the positioning element 46 by a predetermined distance, e.g., providing between about two and five millimeters (2-5 mm) clearance between the distal end 24 and the positioning element 46. Alternatively, the detent 41a may be provided at a predetermined location such that the distal end 24 of the tubular member may be jammed or otherwise extend into the positioning element 46, e.g., by zero to two millimeters (0-2 mm).

The detent 41a may be a raised feature formed or attached to the elongate member 40 at the predetermined location. For example, the detent may be a proximal end of a section of tubing, e.g., heat shrink tubing, a collar, or other sleeve (not shown) attached around the elongate member 40, e.g., by bonding with adhesive, heat shrinking, ultrasonic welding, fusing, crimping, and the like. Alternatively, as shown, the detent 41a may overmolded or otherwise formed directly on the elongate member 40, as desired.

In addition or alternatively, the positioning member 14 and/or advancer member 30 may include one or more elements that engage when the cartridge 16 reaches a predetermined location when advanced along the positioning member 14, e.g., to limit subsequent proximal movement of the advancer member 30 relative to the positioning member 14 when the tubular member 20 is subsequently retracted. For example, the positioning member 14 may include a reduced diameter region (not shown) at a predetermined location, e.g., by providing a larger tube around a smaller inner tube or by machining, etching, or otherwise removing a portion of the tubular body of the positioning member 14 distal to the reduced region. The larger tube may extend from the proximal end of the positioning member 14 to the desired location for the detent, or may simply be a relatively short sleeve or other member (not shown) attached around or to the positioning member 14 at the desired location, e.g., to provide a first ratchet or detent that the advancer member 30 may pass over freely in the distal direction but not subsequently move proximally.

The advancer member 30 may include a living hinge, tab, or other element 37 (also not shown) on the proximal end 32 that may pass freely over the reduced regions, ratchets, and/or other detents on the positioning member 14, yet may be unable to pass proximally back over the reduced region. For example, as shown in FIG. 4B, the positioning member 14 may include a ring, tab, or other raised element, e.g., a first and a second raised element or other detent 41a, 41b, and the advancer member 30 may include a corresponding element (also not shown) that may allow distal advancement but prevent proximal retraction once the advancer member 30 is advanced a predetermined distance.

The first detent 41a may be provided at a predetermined location on the positioning member 14, e.g., a predetermined distance from the positioning element 46 that substantially corresponds to a length of the advancer member 30. As the cartridge 16 (and consequently the advancer member 30) is advanced over the positioning member 14, e.g., until the sealant 2 is disposed adjacent the positioning element 46, the element 37 on the advancer member 30 may pass freely over the first detent 41a, as best seen in FIG. 4B. Thereafter, the element 37 may prevent the advancer member 30 from being retracted again past the first detent 41a, e.g., due to a blunt edge of the element 37 abutting the abrupt distal edge of the first detent 41a. Thus, when the tubular member 20 is retracted after the advancer member 30 has passed entirely over the first detent 41a, the element 37 may prevent the advancer member 30 from retracting with the tubular member 20. Optionally, as shown in FIG. 4B, a second ratchet or detent 41b (shown in phantom) may be provided on the positioning member 14 distal to the first detent 41a, e.g., over which the advancer member 30 may be advanced further, e.g., during compression of the sealant 2 after deployment, as described further below. The second detent 41b may be another tube or other feature (not shown) attached to or formed on the positioning member 14, e.g., that provides a blunt distal edge.

In addition or alternatively, one or more markers may be provided on the apparatus 10, e.g., to identify when components are located at one or more desired positions or otherwise to facilitate use of the apparatus 10. For example, as shown in FIG. 5A, the positioning member 14 may include one or more markers at predetermined locations on the elongate member 40. Such markers may provide visual confirmation when the cartridge 16 has been advanced to a desired distal position, e.g., when the marker(s) 43 emerge from the hub 23 as the cartridge 16 is advanced over the positioning member 14.

Figure 5C:
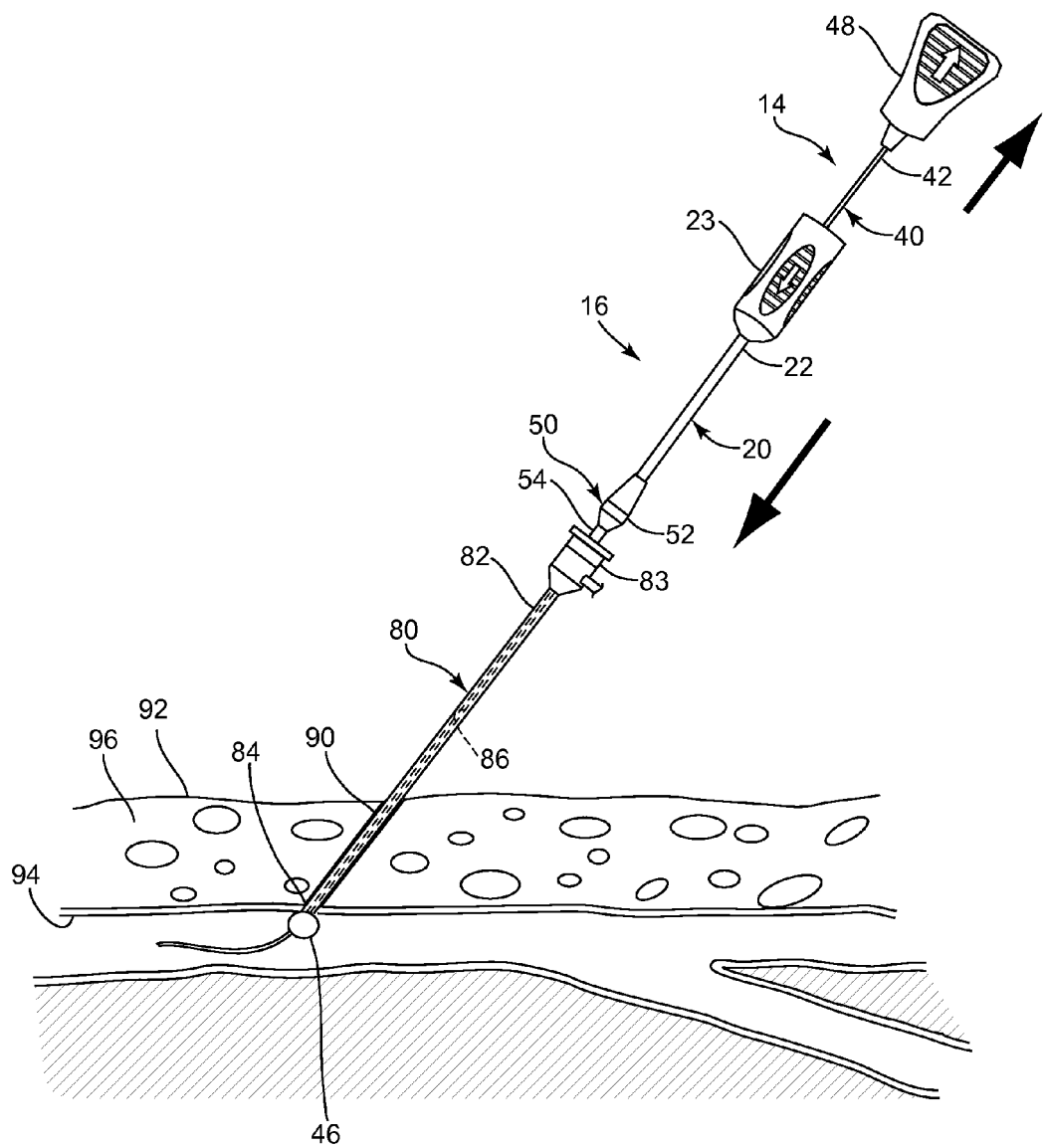
Figure 5D:
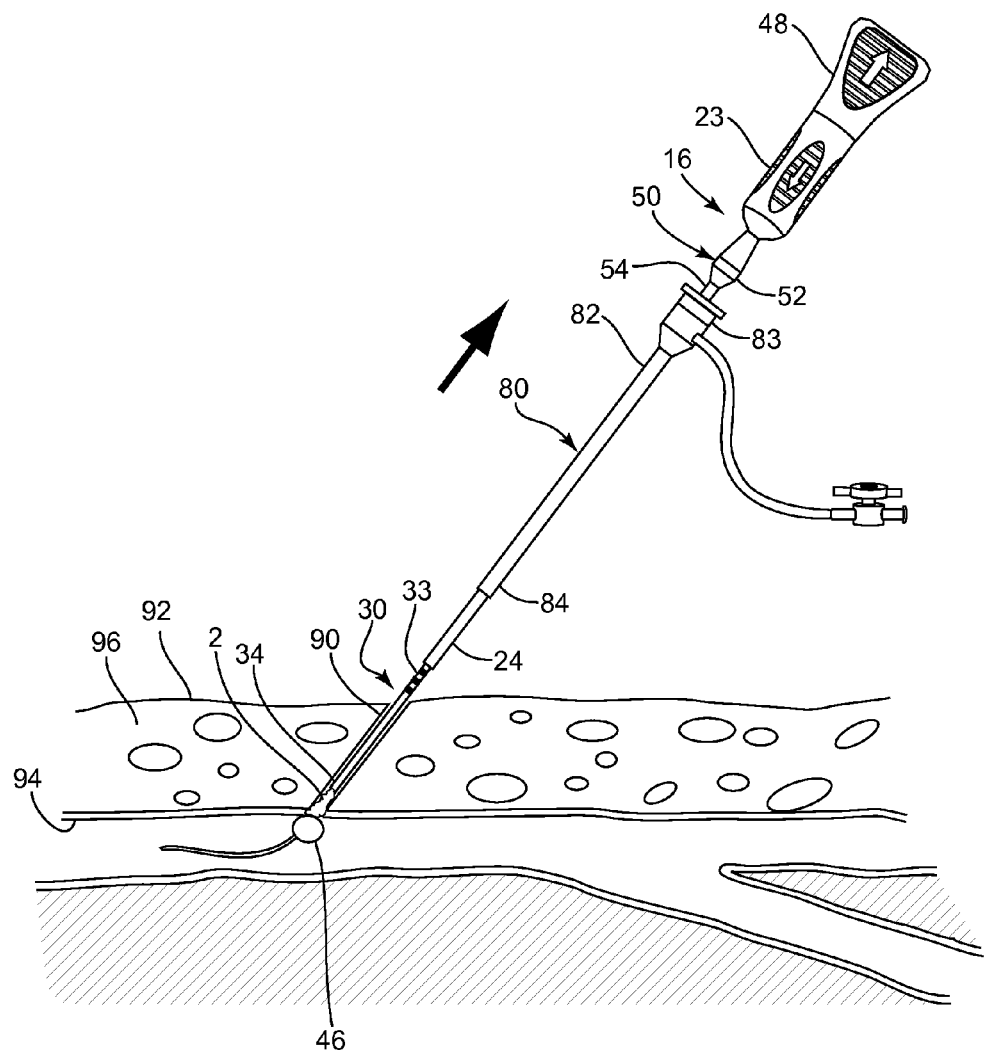

In addition or alternatively, as shown in FIG. 5D, the advancer member 30 may include one or more markers 33 thereon, which may be visible when the cartridge 16 is advanced to a distal position and the tubular member 20 is retracted to expose the sealant 2. These markers 33 may also provide visual guides to inform the user when the advancer member 30 is manipulated, e.g., advanced into a puncture to compress the sealant 2 therein, as described further below.

As best seen in FIGS. 3A, 3B, and 5A-5D, the apparatus 10 is generally used in cooperation with an introducer sheath 80. The introducer sheath 80 may part of a system or kit including the apparatus 10 or may be an independent device. Generally, the introducer sheath 80 includes a proximal end 82, a distal end 84 sized for insertion into a puncture 90 through tissue, and a lumen 86 extending between the proximal and distal ends 82, 84. The introducer sheath 80 may be formed from a substantially rigid, semi-rigid, and/or flexible tubular body including a hub 83 on the proximal end 82. The introducer sheath 80 may have sufficient length to extend from a patient's skin through any intervening tissue into a blood vessel or other body lumen, e.g., having a length between about ten centimeters and twenty centimeters (10-20 cm), and may have an outer diameter between about 1.6 millimeters and five millimeters (1.6-5 mm). The distal end 84 may be tapered and/or may include a substantially atraumatic distal tip 85 for facilitating advancement through a puncture.

The introducer sheath 80 may be formed using known materials and/or methods, e.g., plastic with the tubular body and hub 83 substantially permanently connected together, e.g., using an interference fit, one or more mating connectors (not shown), bonding with adhesive, ultrasonic welding, and the like. The hub 83 generally includes one or more seals, e.g., one or more hemostatic seals (not shown) therein, which may prevent flow of blood or other fluids out of the hub 83 from the lumen 86, yet accommodate insertion of one or more instruments into the lumen 26, such as the positioning member 14 and/or cartridge 16. Optionally, as shown, the hub 83 may include a side port 89 communicating with the lumen 86, e.g., for coupling a source of saline or other fluid (not shown) to the hub 83.

Turning to FIGS. 5A-5D, an exemplary method is shown for sealing a puncture 90, e.g., using the apparatus 10 to deliver a sealant 2, e.g., to achieve hemostasis within the puncture 90. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 80 may be advanced through the puncture 90 into the vessel 94, e.g., over a guide wire placed through the puncture 90 into the vessel 94. The introducer sheath 80 may provide access into the vessel 92 for one or more instruments (not shown), e.g., to allow one or more diagnostic and/or interventional procedures to be performed via the vessel 94. Upon completing the procedure(s) via the vessel 94, any such instrument(s) may be removed from the puncture 90, leaving the introducer sheath 80 extending through the puncture 90 into the vessel 94.

With reference to FIG. 5A, the positioning member 14 may be introduced into and/or through the lumen 46 of the introducer sheath 80, e.g., with the expandable positioning element 46 in a collapsed condition. The cartridge 16, along with the sealant 2 and advancer member 30, may be provided initially on the proximal end 42 of the positioning member 40, e.g., as shown in FIG. 3A. Thus, the distal end 24 of the tubular member 20 may initially be located outside the puncture 90 when the positioning member 40 is advanced into the puncture 90.

Still referring to FIG. 5A, the distal end 44 of the positioning member 140 may be inserted through the puncture 90 (via the introducer sheath 80) and into the vessel 94. Once the positioning element 46 is disposed within the vessel 94, i.e., beyond the distal end 84 of the introducer sheath 80, the positioning element 46 may be expanded to an enlarged condition, as shown. After expanding the positioning element 46, the positioning member 40 may be at least partially withdrawn until the positioning element 46 contacts the wall of the vessel 94, e.g., to substantially seal the vessel 94 from the puncture 90.

In an exemplary method, this may involve a two-step process (although it may be completed in a single substantially continuous action). First, with the positioning element 46 expanded within the vessel 94, the positioning member 14 may be withdrawn until the positioning element 46 contacts the distal end 84 of the introducer sheath 80, which may provide a first tactile feedback to the user (i.e., that the positioning element 46 has contacted the introducer sheath 80, e.g., based upon the increased weight and/or resistance to proximal movement). The positioning member 14 may be withdrawn further until the positioning element 46 contacts the wall of the vessel 94 and resists further withdrawal, thereby providing a second tactile feedback. The introducer sheath 80 may be pulled proximally by the positioning element 46 as the positioning member 14 is withdrawn, e.g., until the distal end 84 of the introducer sheath 80 is withdrawn from the vessel 94 into the puncture 90, as shown in FIG. 5A.

Proximal tension may be applied and/or maintained on the positioning member 14 to hold the positioning element 46 against the wall of the vessel 94, e.g., to seal the puncture 90 from the vessel 94 and/or prevent further removal of the positioning member 14. The proximal tension may be maintained manually or using a tensioner device (not shown) to provide temporary hemostasis, e.g., during the subsequent steps. Exemplary tension devices are disclosed in co-pending application Ser. No. 10/806,952, filed Mar. 22, 2004, the entire disclosure of which is expressly incorporated herein by reference.

Turning to FIGS. 3B and 5B, the cartridge 16 (carrying the sealant 2) may be advanced distally over the positioning member 14 into the puncture 90. For example, FIGS. 3A and 3B show the cartridge 16, carrying the sleeve 50 over the distal end 24 of the tubular member 20, being advanced distally over the positioning member 14 towards the introducer sheath 80. As the cartridge 16 is advanced, the sleeve 50 may contact the introducer sheath 80, which may prevent further advancement of the sleeve 50. For example, the distal portion 54 of the sleeve 50 may at least partially enter the hub 83 of the introducer sheath 80 and the proximal portion 52 of the sleeve 50 may abut the hub 83, as shown in FIGS. 5B and 5C, thereby preventing further advancement of the sleeve 50. If the sleeve 50 is releasably attached to the tubular member 20, advancement of the cartridge 16 to this point may release the sleeve 50 from the tubular member 20.

The cartridge 16 may be further advanced into the introducer sheath 80 toward the positioning element 46, whereupon the sleeve 50 may remain substantially stationary relative to the introducer sheath 80 and, consequently, slide proximally over the tubular member 20. Thus, the distal end 24 of the tubular member 20 may exit the distal portion 54 of the sleeve 50 and enter the introducer sheath lumen 86. Optionally, the distal portion 54 of the sleeve 50 may have sufficient length to at least partially open the valve(s) within the introducer sheath hub 83, e.g., to facilitate the distal end 24 of the tubular member 20 being advanced into the introducer sheath lumen 86. Thus, the sleeve 50 may protect the slitted distal tip 25 of the tubular member 20 until the distal tip 25 passes into the hub 83 and/or lumen 86 of the introducer sheath 80.

The cartridge 16 may be advanced until a component of the cartridge 16 encounters a stop on the positioning member 14, thereby preventing further advancement of the cartridge 16 and/or spacing the sealant 2 a predetermined distance from the positioning element 46, e.g., about zero to five millimeters (0-5 mm) from the positioning element 46 or zero to two millimeters (0-2 mm) into or beyond the positioning member 14. For example, as shown in FIG. 4B, the cartridge 16 may be advanced until the detent 41a on the positioning member 14 enters the recess 23b in the cartridge hub 23. Alternatively, if the cooperating features 31, 23b are omitted, the cartridge 16 may be advanced into the introducer sheath 80 until the distal end 24 contacts the expanded positioning element 46 (not shown), which may provide tactile feedback that the cartridge 16 has been advanced sufficiently, or the sealant 2 is otherwise positioned within the puncture 90.

Thereafter, as shown in FIG. 5D, the tubular member 20 of the cartridge 16 may be retracted, e.g., by pulling proximally on the hub 83 of the introducer sheath 80, to withdrawn the introducer sheath 80 and tubular member 20 from the puncture 90 and expose the sealant 2 within the puncture beyond the introducer sheath distal end 84. Optionally, the sleeve 50 may include one or more locking elements (not shown) that may couple the introducer sheath 80 to the sleeve 50, similar to the embodiments disclosed in application Ser. No. 11/864,835, filed Sep. 28, 2007, and published as U.S. Publication No. 2009/0088793, the entire disclosure of which is expressly incorporated by reference herein. Thus, in this alternative, if the user pulls proximally on the sleeve 50 rather than the introducer sheath 80, the introducer sheath 80 and tubular member 20 may still be withdrawn together from the puncture 90.

As the tubular member 20 is retracted, the advancer member 30 may prevent substantial proximal movement of the sealant 2, thereby exposing the sealant 2 within the puncture 90, as shown in FIG. 5D. For example, as described above, as the cartridge 16 is advanced, the feature(s) 37 on the proximal end 32 of the advancer member 30 may pass over the reduced region or first detent 41a of the positioning member 14, as shown in FIG. 4B, thereby preventing subsequent proximal withdrawal of the advancer member 30 relative to the positioning member 14. Thus, when the cartridge 16 is then refracted, the element 37 on the advancer member 30 may abut the blunt distal edge of the reduced region or first detent 41a, thereby preventing substantial proximal movement of the advancer member 30, and the sealant 2 adjacent the distal end 34 of the advancer member 30.

When the sealant 2 is exposed within the puncture 90, the sealant 2 may be exposed to blood and/or other body fluids within the puncture 90. This exposure may cause the sealant 2 to absorb fluid and/or otherwise expand within the puncture 90, e.g., to provide hemostasis. If desired, once the sealant 2 is exposed within the puncture 90, the advancer member 30 may be advanced to compress or tamp the sealant 2, e.g., against the positioning element 46. Optionally, the advancer member 30 may include one or more markers 33, e.g., on or adjacent the proximal end 32, and the advancer member 30 may be advanced into the puncture 90 a desired distance, which may be confirmed by monitoring the markers 33. In addition or alternatively, as shown in FIG. 4B, the positioning member 14 may include a second detent 41b over which the advancer member 30 may pass when advanced a predetermined distance. The second detent 41b may provide an audible confirmation that the advancer member 30 has been advanced the predetermined distance (in addition or instead of the visible confirmation provided by the markers 33). In addition, the second detent 41b may ensure that the advancer member 30 is not subsequently withdrawn once advanced the predetermined distance.

Once the sealant 2 has been exposed for sufficient time and/or tamped by the advancer member 30, the positioning element 46 may be collapsed, and the positioning member 14 withdrawn from the vessel 94 and puncture 90, e.g., pulling the collapsed positioning element 46 through the sealant 2 and advancer member 30. The advancer member 30 may be maintained substantially stationary during withdrawal of the positioning member 14, e.g., to prevent migration and/or dislodgment of the sealant 2 within the puncture 90. Once the positioning member 14 is completely removed, the advancer member 30 may be removed from the puncture 90, leaving the sealant 2 within the puncture 90.

Optionally, after removing the positioning member 14, liquid hydrogel or other sealing compound, or other material may be delivered into the puncture 90, e.g., above and/or around the sealant 2, to assist in achieving hemostasis. For example, such material may be delivered via the lumen 36 of the advancer member 30 and/or by introducing another delivery device (not shown) into the puncture 90, e.g., after removing the advancer member 30.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for sealing a puncture extending through tissue, comprising:

an introducer sheath comprising a proximal end including a hub, a distal end sized for insertion through a puncture through tissue, and a lumen extending between the proximal and distal ends;

a positioning member comprising an elongate member including proximal and distal ends, a housing on the proximal end, and an expandable positioning element on the distal end; and a cartridge advanceable along the positioning member from a proximal position adjacent the housing to a distal position, the cartridge comprising:

a) a tubular member comprising a proximal end, a distal end sized for insertion into the introducer sheath lumen, and a lumen extending between the tubular member proximal and distal ends;

b) a sealant disposed within the tubular member lumen;

c) an advancer member disposed within the tubular member lumen for exposing the sealant distally from the tubular member lumen when the tubular member is retracted proximally relative to the advancer member; and d) a sleeve slidably disposed over the tubular member distal end, at least a portion of the sleeve sized to abut the introducer sheath hub such that, when the tubular member is advanced from the proximal position to the distal position, the tubular member distal end enters the introducer sheath lumen through the hub while the sleeve is stopped by the introducer sheath hub and slides over the tubular member to expose the tubular member distal end within the introducer sheath lumen, wherein the sealant is disposed within the tubular member adjacent the tubular member distal end, and wherein the tubular member comprises a slitted distal tip comprising slits that allow the distal tip to open upon hydration and expansion of the sealant while the tubular member is located within the lumen of the introducer sheath;

wherein the sleeve comprises an inner surface configured to provide different frictional interference with an outer surface of the tubular member to allow proximal movement and resist distal movement of the sleeve over the tubular member.

2. The system of claim 1, wherein the sleeve comprises a distal portion free of locking elements and sized to enter the introducer sheath hub without locking to the introducer sheath hub when the cartridge is advanced towards the distal position and a proximal portion that abuts the introducer sheath hub to prevent the entire sleeve from entering the introducer sheath lumen.

3. The system of claim 2, wherein the introducer sheath hub comprises a hemostatic valve therein, and wherein the sleeve distal portion at least partially opens the valve when the cartridge is advanced towards the distal position to facilitate the tubular member distal end entering the introducer sheath lumen.

4. The system of claim 1, wherein the slitted distal tip comprises a slit having a length longer than the sealant to facilitate exposure of the sealant from the tubular member distal end when the tubular member is retracted proximally after being advanced to the distal position.

5. The system of claim 1, wherein at least one of the positioning member and the cartridge comprise one or more features that limit further distal movement of the tubular member when the cartridge is advanced from the proximal position to the distal position.

6. The system of claim 5, wherein the one or more features are located to prevent further distal movement of the tubular member when the tubular member distal end is spaced a predetermined distance from the positioning element.

7. The system of claim 1, wherein the sleeve has a relatively short length relative to the tubular member.

8. The system of claim 1, further comprising cooperating elements on the advancer member and the positioning member that limit subsequent proximal movement of the advancer member relative to the positioning member after the cartridge is advanced to the distal position.

9. The system of claim 8, wherein the positioning member is removable through the advancer member with the positioning element collapsed, thereby allowing the positioning member to be withdrawn from a puncture before the advancer member is withdrawn such that advancer member prevents the plug from moving proximally while the positioning member is withdrawn.

10. The system of claim 8, wherein the cooperating elements comprise a first detent on the positioning member over which the advancer member passes when the cartridge is advanced to the distal position, and one or more features on a proximal end of the advancer member that prevent the advancer member from subsequent proximal movement back over the first detent.

11. The system of claim 10, further comprising a second detent on the positioning member distal to the first detent, the advancer member advanceable over the second detent to compress the sealant between a distal end of the advancer member and the expandable positioning element after the cartridge is withdrawn to expose the sealant within a puncture.

12. An apparatus for sealing a puncture extending through tissue having an introducer sheath therein that includes a proximal end including a hub, a distal end, and a lumen extending therebetween, the apparatus comprising:

a positioning member comprising an elongate member including proximal and distal ends, a housing on the proximal end, and an expandable positioning element on the distal end; and a cartridge advanceable along the positioning member from a proximal position adjacent the housing to a distal position, the cartridge comprising:

a) a tubular member comprising a proximal end, a distal end sized for insertion into the introducer sheath lumen, and a lumen extending between the tubular member proximal and distal ends;

b) a sealant disposed within the tubular member lumen adjacent the tubular member distal end;

c) an advancer member disposed within the tubular member lumen for exposing the sealant distally from the tubular member lumen when the tubular member is retracted proximally relative to the advancer member; and d) a sleeve slidably disposed over the tubular member distal end, at least a portion of the sleeve sized to abut to the introducer sheath hub without coupling the sleeve to the introducer sheath hub such that, when the tubular member is advanced from the proximal position to the distal position, the tubular member distal end enters the introducer sheath lumen through the hub without locking to the hub while the sleeve is stopped by the introducer sheath hub and slides over the tubular member to expose the tubular member distal end within the introducer sheath lumen;

wherein the sleeve comprises an inner surface configured to provide different frictional interference with an outer surface of the tubular member to allow proximal movement and resist distal movement of the sleeve over the tubular member.

13. The apparatus of claim 12, wherein the sleeve comprises a distal portion sized to enter the introducer sheath hub when the cartridge is advanced towards the distal position and a proximal portion that abuts the introducer sheath hub to prevent the entire sleeve from entering the introducer sheath lumen.

14. The apparatus of claim 13, wherein the introducer sheath hub comprises a hemostatic valve therein, and wherein the sleeve distal portion at least partially opens the valve when the cartridge is advanced towards the distal position to facilitate the tubular member distal end entering the introducer sheath lumen.

15. The apparatus of claim 12, wherein the sealant is disposed within the tubular member adjacent the tubular member distal end, and wherein the tubular member comprises a slitted distal tip to facilitate exposure of the sealant from the tubular member distal end when the tubular member is retracted proximally after being advanced to the distal position.

16. The apparatus of claim 12, wherein at least one of the positioning member and the cartridge comprise one or more features that limit distal movement of the tubular member when the cartridge is advanced from the proximal position to the distal position.

17. The apparatus of claim 16, wherein the one or more features are located to prevent further distal movement of the tubular member when the tubular member distal end is spaced a predetermined distance from the positioning element.

18. The apparatus of claim 12, further comprising cooperating elements on the advancer member and the positioning member that limit subsequent proximal movement of the advancer member relative to the positioning member after the cartridge is advanced to the distal position.

19. The apparatus of claim 18, wherein the positioning member is removable through the advancer member with the positioning element collapsed, thereby allowing the positioning member to be withdrawn from a puncture before the advancer member is withdrawn such that advancer member prevents the plug from moving proximally while the positioning member is withdrawn.

20. The system of claim 18, wherein the cooperating elements comprise a first detent on the positioning member over which the advancer member passes when the cartridge is advanced to the distal position, and one or more features on a proximal end of the advancer member that prevent the advancer member from subsequent proximal movement back over the first detent.

21. The system of claim 20, further comprising a second detent on the positioning member distal to the first detent, the advancer member advanceable over the second detent to compress the sealant between a distal end of the advancer member and the expandable positioning element after the cartridge is withdrawn to expose the sealant within a puncture.

22. The apparatus of claim 12, wherein the sleeve has a relatively short length relative to the tubular member.

23. The apparatus of claim 12, wherein a distal portion of the sleeve free of locking elements is sized to enter the introducer sheath without coupling the sleeve to the introducer sheath hub.

24. The apparatus of claim 12, wherein the distal portion of the sleeve has a smooth outer surface that allows the distal portion to enter the introducer sheath hub without coupling the sleeve to the introducer sheath hub.

25. A system for sealing a puncture extending through tissue, comprising:
  an introducer sheath comprising a proximal end including a hub, a distal end sized for insertion through a puncture through tissue, and a lumen extending between the proximal and distal ends;
  a positioning member comprising an elongate member including proximal and distal ends, a housing on the proximal end, and an expandable positioning element on the distal end; and
  a cartridge advanceable along the positioning member from a proximal position adjacent the housing to a distal position, the cartridge comprising:
    a) a tubular member comprising a proximal end, a distal end sized for insertion into the introducer sheath lumen, and a lumen extending between the tubular member proximal and distal ends;
    b) a sealant disposed within the tubular member lumen;
    c) an advancer member disposed within the tubular member lumen for exposing the sealant distally from the tubular member lumen when the tubular member is retracted proximally relative to the advancer member; and
    d) a sleeve slidably disposed over the tubular member distal end, at least a portion of the sleeve sized to abut the introducer sheath hub such that, when the tubular member is advanced from the proximal position to the distal position, the tubular member distal end enters the introducer sheath lumen through the hub while the sleeve is stopped by the introducer sheath hub and slides over the tubular member to expose the tubular member distal end within the introducer sheath lumen, the sleeve comprising an inner surface configured to provide different frictional interference with an outer surface of the tubular member to allow proximal movement and resist distal movement of the sleeve over the tubular member.

26. The system of claim 25, wherein the sleeve comprises a distal portion sized to enter the introducer sheath hub when the cartridge is advanced towards the distal position and a proximal portion that abuts the introducer sheath hub to prevent the entire sleeve from entering the introducer sheath lumen.

* * * * *